United States Patent
Skala et al.

(10) Patent No.: US 12,023,676 B2
(45) Date of Patent: Jul. 2, 2024

(54) SYSTEMS AND METHODS FOR SORTING T CELLS BY ACTIVATION STATE

(71) Applicant: Wisconsin Alumni Research Foundation, Madison, WI (US)

(72) Inventors: Melissa Caroline Skala, Middleton, WI (US); Alexandra Jule Walsh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/855,929

(22) Filed: Jul. 1, 2022

(65) Prior Publication Data

US 2023/0116814 A1 Apr. 13, 2023

Related U.S. Application Data

(63) Continuation of application No. 16/554,327, filed on Aug. 28, 2019, now Pat. No. 11,376,593.

(60) Provisional application No. 62/724,428, filed on Aug. 29, 2018.

(51) Int. Cl.
| | |
|---|---|
| *B01L 3/00* | (2006.01) |
| *A61K 35/17* | (2015.01) |
| *C12N 5/00* | (2006.01) |
| *C12N 5/0783* | (2010.01) |
| *G01N 21/64* | (2006.01) |

(52) U.S. Cl.
CPC ........ *B01L 3/502761* (2013.01); *A61K 35/17* (2013.01); *C12N 5/0087* (2013.01); *C12N 5/0636* (2013.01); *G01N 21/6408* (2013.01); *G01N 21/6428* (2013.01); *B01L 2200/0652* (2013.01); *B01L 2200/143* (2013.01); *B01L 2300/0663* (2013.01); *B01L 2300/0864* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2011/0020459 A1* | 1/2011 | Achrol | B01L 3/502753 435/287.1 |
| 2012/0276578 A1 | 11/2012 | Stringari et al. | |
| 2018/0141048 A1* | 5/2018 | Kung | C12N 5/0018 |

FOREIGN PATENT DOCUMENTS

| | | |
|---|---|---|
| JP | 2009533160 A | 9/2009 |
| JP | 2010233843 A | 10/2010 |
| JP | 2011185841 A | 9/2011 |
| JP | 2011185843 A | 9/2011 |
| JP | 2011185844 A | 9/2011 |

(Continued)

OTHER PUBLICATIONS

Abadi, M. et al. TensorFlow: Large-Scale Machine Learning on Heterogeneous Systems (2015). arXiv preprint arXiv:1603.04467 (2016).

(Continued)

*Primary Examiner* — Neil N Turk
(74) *Attorney, Agent, or Firm* — Quarles & Brady, LLP (57) ABSTRACT

Systems and methods for sorting T cells are disclosed. Autofluorescence data is acquired from individual cells. An activation value is computed using one or more autofluorescence endpoints as an input. The one or more autofluorescence endpoints includes NAD(P)H shortest fluorescence lifetime amplitude component ($\alpha_1$).

9 Claims, 3 Drawing Sheets

(56) References Cited

FOREIGN PATENT DOCUMENTS

| JP | 2015108549 A | 6/2015 |
|---|---|---|
| JP | 2016505263 A | 2/2016 |

OTHER PUBLICATIONS

Adebayo, J, et al. "Sanity checks for saliency maps." Advances in Neural Information Processing Systems. 2018.

Carpenter, A. E. et al. CellProfiler: image analysis software for identifying and quantifying cell phenotypes. Genome Biol. 7, R100 (2006). DOI 10.1186/gb-2006-7-10-r100.

Chen, C. L. et al. Deep Learning in Label-free Cell Classification. Sci. Reports 6 (2016). DOI 10.1038/srep21471.

Deng, Jia, et al. "Imagenet: A large-scale hierarchical image database." 2009 IEEE conference on computer vision and pattern recognition. IEEE, 2009.

Godinez, W. J., et al. A multi-scale convolutional neural network for phenotyping high-content cellular images. Bioinformatics 33, 2010-2019 (2017). DOI 10.1093/bioinformatics/btx069.

Guo, B. et al. High-throughput, label-free, single-cell, microalgal lipid screening by machine learning-equipped optofluidic time-stretch quantitative phase microscopy. Cytom. Part A 91, 494-502 (2017). DOI 10.1002/cyto.a.23084.

Guo, C., et al. On Calibration of Modern Neural Networks. arXiv:1706.04599 (2017).

Lecun, Y., et al. Gradient-based learning applied to document recognition. Proc. IEEE 86, 2278-2324 (1998). DOI 10.1109/5.726791.

Maaten, L. v. d. et al. Visualizing data using t-sne. J. machine learning research 9, 2579-2605 (2008).

Marek-Trzonkowska, N. et al. Administration of CD4+ CD25highcd127—Regulatory T Cells Preserves—Cell Function in Type 1 Diabetes in Children. Diabetes Care 35, 1817-1820 (2012). DOI 10.2337/dc12-0038.

Nitta, N. et al. Intelligent Image-Activated Cell Sorting. Cell 175, 266-276.e13 (published online Aug. 27, 2018). DOI 10.1016/j.cell.2018.08.028.

Pardoll, D. M. The blockade of immune checkpoints in cancer immunotherapy. Nat. Rev. Cancer 12, 252-264 (2012). DOI 10.1038/nrc3239.

Pavillon, N., et al. Noninvasive detection of macrophage activation with single-cell resolution through machine learning. Proc. Natl. Acad. Sci. 115, E2676-E2685 (Mar. 6, 2018). DOI 10.1073/pnas.1711872115.

Pedregosa, F. et al. Scikit-learn: Machine Learning in Python. J. Mach. Learn. Res. 12, 2825-2830 (2011).

Project Jupyter et al. Binder 2.0—Reproducible, interactive, sharable environments for science at scale. Proc. 17th Python Sci. Conf. 113-120 (Jan. 2018). DOI 10.25080/Majora-4af1f417-011.

Restifo, N. P., et al. Adoptive immunotherapy for cancer: harnessing the T cell response. Nat. Rev. Immunol. 12, 269-281 (2012). DOI 10.1038/nri3191.

Shields et al., "Microfluidic cell sorting: a review of the advances in the separation of cells from debulking to rare cell isolation," Lab Chip, Mar. 7, 2015; 15(5): 1230-49.

Simonyan, K., et al. Deep Inside Convolutional Networks: Visualising Image Classification Models and Saliency Maps. arXiv:1312.6034 (2013).

Szegedy, C., et al. Rethinking the Inception Architecture for Computer Vision. arXiv:1512.00567 [cs] (2015).

Szulczewski, J. M. et al. In Vivo Visualization of Stromal Macrophages via label-free FLIM based metabolite imaging. Sci. Reports 6 (2016). DOI 10.1038/srep25086.

Kluyver, T. et al. Jupyter Notebooks—a publishing format for reproducible computational workflows. Stand Alone 87-90(2016). DOI 10.3233/978-1-61499-649-1-87.

Weigert, M. et al. Content-Aware Image Restoration: Pushing the Limits of Fluorescence Microscopy. bioRxiv (Jul. 2018). DOI 10.1101/236463.

Kelly et al., J of Innovative Optical Health Sciences, 2014, 7(5): 1450025 pp. 1-15.

Linghao Hu et al., "Fluorescence intensity and lifetime redox ratios detect metabolic perturbations in T cells", Biomedical Optics Express, Sep. 16, 2020, vol. 11, No. 10, p. 5674, DOI: 10.1364/BOE.401935.

Takakazu Nakabayashi and Nobuhiro Ohta, "Observation of Living Cells Using Autofluorescence Lifetime Imaging", Seibutsu Butsuri, 2013, vol. 53, No. 3, p. 166-169.

\* cited by examiner

SYSTEMS AND METHODS FOR SORTING T CELLS BY ACTIVATION STATE

CROSS-REFERENCE TO RELATED APPLICATIONS

This application is a continuation of U.S. application Ser. No. 16/554,327, filed Aug. 28, 2019, which application claims the benefit of U.S. Provisional Patent Application No. 62/724,428, filed Aug. 29, 2018, which is incorporated by reference herein in its entirety for all purposes.

STATEMENT REGARDING FEDERALLY FUNDED RESEARCH

This invention was made with government support under CA205101 awarded by the National Institutes of Health. The government has certain rights in the invention.

BACKGROUND

One new cancer treatment being studied is CAR T cell (Chimeric Antigen Receptor T cell) therapy. CAR T cell therapy uses a patient's own cells and "re-engineers" them to fight cancer. It is a very complex treatment. Collecting and altering the cells is difficult, and CAR T cell therapy often causes very severe side effects. At this time, it is only offered at a few major cancer centers. To date, most of the patients treated with CAR T cell have been people with blood cancers.

The procedure starts with removing the patient's own T cells from their blood and sending them to a lab where they are altered to produce proteins called chimeric antigen receptors (CARs) on the surface of the cells. These special receptors allow the T cells to help identify and attack cancer cells. The "super-charged" T cells are multiplied and grown at the lab, then frozen and shipped back to Hospital, where they re-inject these treated CAR T cells back into the patient's blood.

Current methods to determine T cell activation include flow cytometry, immunofluorescence imaging, and immunohistochemistry but these methods require contrast agents and may require tissue or cell fixation. A need exists for system and methods for sorting T cells by activation state in a fashion that allows the sorted T cells to be used in subsequent procedures, such as CAR T cell therapy.

SUMMARY

In one aspect, the present disclosure provides a T cell sorting device. The T cell sorting device includes a cell sorting pathway, a single-cell autofluorescence detector, a processor, and a non-transitory computer-readable medium. The cell sorting pathway includes an inlet, an observation zone, and a cell sorter. The observation zone is coupled to the inlet downstream of the inlet. The observation zone is configured to present T cells for individual autofluorescence interrogation. The cell sorter has a sorter inlet and at least two sorter outlets. The cell sorter is coupled to the observation zone via the sorter inlet downstream of the observation zone. The cell sorter is configured to selectively direct a cell from the sorter inlet to one of the at least two sorter outlets based on a sorter signal. The single-cell autofluorescence detector is configured to acquire an autofluorescence data set from a T cell positioned in the observation zone. The single-cell autofluorescence detector is configured to acquire autofluorescence lifetime information for each autofluorescence data set. The processor is in electronic communication with the cell sorter and the single-cell autofluorescence detector. The non-transitory computer-readable medium has stored thereon instructions that, when executed by the processor, cause the processor to: a) receive the autofluorescence data set; and b) provide the sorter signal to the cell sorter based on an activation value. The sorter signal directs the cell sorter to selectively direct the T cell to a first outlet of the at least two sorter outlets when the activation value exceeds a predetermined threshold and to a second outlet of the at least two sorter outlets when the activation value is less than or equal to the predetermined threshold. The activation value is computed using at least one metabolic endpoint of the autofluorescence data set for the T cell as an input. The at least one metabolic endpoint includes reduced nicotinamide adenine dinucleotide (phosphate) (NAD(P)H) shortest autofluorescence lifetime amplitude component ($\alpha_1$).

In another aspect, the present disclosure provides a method of sorting T cells. The method includes: a) receiving a population of T cells having unknown activation status; b) acquiring an autofluorescence data set for each T cell of the population of T cells, each autofluorescence data set including autofluorescence lifetime information; and c) physically isolating a first portion of the population of T cells from a second portion of the population of T cells based on an activation value, wherein each T cell of the population of T cells is placed into the first portion when the activation value exceeds a predetermined threshold and into the second portion when the activation value is less than or equal to the predetermined threshold, wherein the activation value is computed using at least one metabolic endpoint of the autofluorescence data set for each T cell of the population of T cells as an input, wherein the at least one metabolic endpoint includes NAD(P)H $\alpha_1$.

In a further aspect, the present disclosure provides a method of administering activated T cells to a subject in need thereof. The method includes: physical isolating a first portion of a population of T cells from a second portion of the population of T cells based on an activation value, wherein each T cell of the population of T cells is placed into the first portion when the activation value exceeds a predetermined threshold and into the second portion when the activation value is less than or equal to the predetermined threshold, wherein the activation value is computed using at least one metabolic endpoint of an autofluorescence data set for each T cell of the population of T cells as an input, wherein the at least one metabolic endpoint includes NAD(P)H $\alpha_1$; and introducing the first portion of the population of T cells to the subject. The method can further include modifying the first portion of the population of T cells prior to the introducing to the subject. The modification can be modification to include a chimeric antigen receptor.

DETAILED DESCRIPTION

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to modifying biological molecules are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

As used herein, the terms "activated" and "activation" refer to T cells that are CD3+, CD4+, and/or CD8+.

As used herein, the term "FAD" refers to flavin adenine dinucleotide.

As used herein, the term "memory" includes a non-volatile medium, e.g., a magnetic media or hard disk, optical storage, or flash memory; a volatile medium, such as system memory, e.g., random access memory (RAM) such as DRAM, SRAM, EDO RAM, RAMBUS RAM, DR DRAM, etc.; or an installation medium, such as software media, e.g., a CD-ROM, or floppy disks, on which programs may be stored and/or data communications may be buffered. The term "memory" may also include other types of memory or combinations thereof.

As used herein, the term "NAD(P)H" refers to reduced nicotinamide adenine dinucleotide and/or reduced nicotinamide dinucleotide phosphate.

As used herein, the term "processor" may include one or more processors and memories and/or one or more programmable hardware elements. As used herein, the term "processor" is intended to include any of types of processors, CPUs, microcontrollers, digital signal processors, or other devices capable of executing software instructions.

As used herein, the term "redox ratio" or "optical redox ratio" refers to a ratio of NAD(P)H fluorescence intensity to FAD fluorescence intensity; a ratio of FAD fluorescence intensity to NAD(P)H fluorescence intensity; a ratio of NAD(P)H fluorescence intensity to any arithmetic combination including FAD fluorescence intensity; or a ratio of FAD fluorescence intensity to any arithmetic combination including NAD(P)H fluorescence intensity.

Autofluorescence endpoints include photon counts/intensity and fluorescence lifetimes. The fluorescence lifetime of cells can be a single value, the mean fluorescence lifetime, or compromised from the lifetime values of multiple subspecies with different lifetimes. In this case, multiple lifetimes and lifetime component amplitude values are extracted. Both NAD(P)H and FAD can exist in quenched (short lifetime) and unquenched (long lifetime) configurations; therefore, the fluorescence decays of NAD(P)H and FAD are fit to two components. Generally, NADH and FAD fluorescence lifetime decays are fit to a two component exponential decay, $I(t)=\alpha_1 e^{-t/\tau_1}+\alpha_2 e^{-t/\tau_2}+C$, where $I(t)$ is the fluorescence intensity as a function of time, $t$, after the laser pulse, $\alpha_1$ and $\alpha_2$ are the fractional contributions of the short and long lifetime components, respectively (i.e., $\alpha_1+\alpha_2=1$), $\tau_1$ and $\tau_2$ are the short and long lifetime components, respectively, and C accounts for background light. However, the lifetime decay can be fit to more components (in theory any number of components, although practically up to ~5-6) which would allow quantification of additional lifetimes and component amplitudes. By convention lifetimes and amplitudes are numbered from short to long, but this could be reversed. A mean lifetime can be computed from the lifetime components, ($\tau_m=\alpha_1\tau_1+\alpha_2\tau_2$ . . . ). Fluorescence lifetimes and lifetime component amplitudes can also be approximated from frequency domain data and gated cameras/detectors. For gated detection, $\alpha_1$ could be approximated by dividing the detected intensity at early time bins by later time bins. Alternatively, fluorescence anisotropy can be measured by polarization-sensitive detection of the autofluorescence, thus identifying free NAD(P)H as the short rotational diffusion time in the range of 100-700 ps.

NAD(P)H $\alpha_1$ refers to the contribution of free NAD(P)H and is the shortest lifetime that is not dominated (i.e., greater than 50%) by instrument response and/or scattering. NAD(P)H $\alpha_1$ is the contribution associated with NAD(P)H lifetime values from 200-1500 ns, from 200-1000 ns, or from 200-600 ns. For clarity, a claim herein including features related to a "shortest" lifetime cannot be avoided by defining the lifetime values to include a sacrificial shortest lifetime that is dominated by instrument response and/or scattering.

The various aspects may be described herein in terms of various functional components and processing steps. It should be appreciated that such components and steps may be realized by any number of hardware components configured to perform the specified functions.

Methods

This disclosure provides a variety of methods. It should be appreciated that various methods are suitable for use with other methods. Similarly, it should be appreciated that various methods are suitable for use with the systems described elsewhere herein. When a feature of the present disclosure is described with respect to a given method, that feature is also expressly contemplated as being useful for the other methods and systems described herein, unless the context clearly dictates otherwise.

Figure 1:
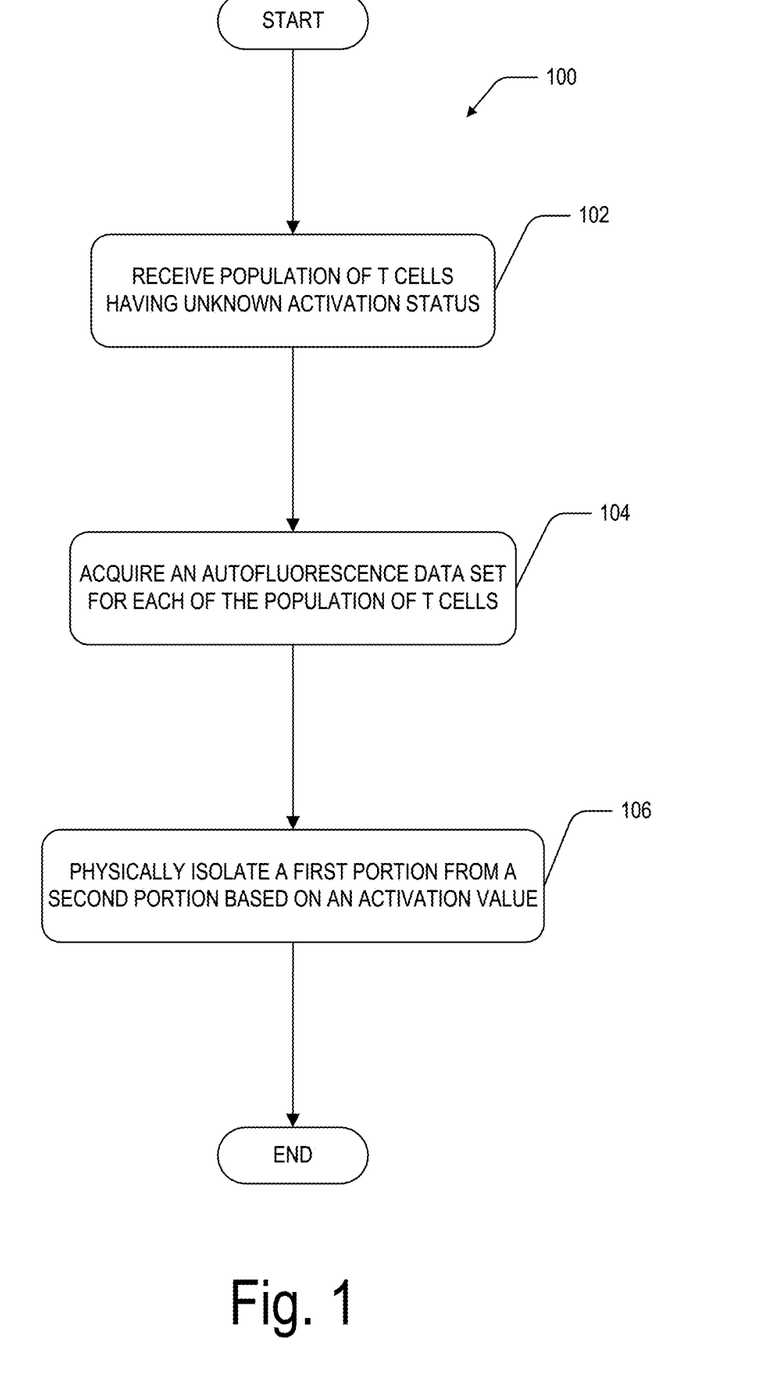
FIG. 1 is a flowchart illustrating a method, in accordance with an aspect of the present disclosure.

Referring to FIG. 1, the present disclosure provides a method 100 of sorting T cells. At process block 102, the method 100 includes receiving a population of T cells having unknown activation status. At process block 104, the method 100 includes acquiring an autofluorescence data set for each T cell of the population of T cells. At process block 106, the method 100 includes physically isolating a first portion of the population of T cells from a second portion of the population of T cells based on an activation value.

The autofluorescence data set acquired at process block 104 includes lifetime information and can be acquired in a variety of ways, as would be understood by one having ordinary skill in the spectroscopic arts with knowledge of this disclosure and their own knowledge from the field. For example, the autofluorescence data can be acquired from fluorescence decay data. As another example, the autofluorescence data can be acquired by gating a detector (a camera, for instance) to acquire data at specific times throughout a decay in order to approximate the autofluorescence endpoints described herein. As yet another example, a frequency domain approach can be used to measure lifetime. Alternatively, fluorescence anisotropy can be measured by polarization-sensitive detection of the autofluorescence, thus identifying free NAD(P)H as the short rotational diffusion time in the range of 100-700 ps. The specific way in which autofluorescence data is acquired is not intended to be limiting to the scope of the present invention, so long as the lifetime information necessary to determine the autofluorescence endpoints necessary for the methods described herein can be suitably measured, estimated, or determined in any fashion.

The physically isolating of process block 106 is in response to an activation value determined from the acquired autofluorescence data. If the activation value exceeds a predetermined threshold for a given T cell, then that T cell is placed into the first portion. If the activation value is less than or equal to the predetermined threshold for the given T cell, then that T cell is placed into the second portion. The result of this physically isolating is that the first portion of the population of T cells is significantly enriched in activated T cells, whereas the second portion of the population of T cells is significantly depleted of activated T cells.

In some cases, the physically isolating of process block 106 can include isolating cells into three, four, five, six, or more portions. In these cases, the different portions will be separated by a number of predetermined thresholds that is one less than the number of portions (i.e., three portions=two predetermined thresholds). The portion whose activation value exceeds all of the predetermined thresholds (i.e., exceeds the highest threshold) contains the greatest concentration of activated T cells. The portion whose activation value fails to exceed any of the predetermined thresholds (i.e., fails to exceed the lowest threshold) contains the lowest concentration of activated T cells. Using multiple predetermined thresholds can afford the preparation of portions of the population of T cells that have extremely high or extremely low concentrations of activated T cells.

The activation value is computed using at least one metabolic endpoint of the autofluorescence data set for each T cell of the population of T cells as an input. The activation value is computed using an equation that is generated by a machine learning process on data for a population of T cells having a known activation state using the at least one metabolic endpoint as a variable. In some cases, the activation value can have different predictability for the different kinds of activation (i.e., can be more predictive of CD8+ activation than CD4+ activation or vice versa).

The at least one metabolic endpoint includes the NAD(P)H shortest lifetime amplitude component or NAD(P)H $\alpha_1$. The at least one metabolic endpoint can also optionally include one or more of the following: NAD(P)H fluorescence intensity; FAD fluorescence intensity; an optical redox ratio (i.e., a combination of NAD(P)H and FAD intensities such as NAD(P)H/FAD or FAD/NAD(P)H or FAD/[NAD(P)H+FAD] or NAD(P)H/[NAD(P)H+FAD], see definition above); NAD(P)H second shortest lifetime amplitude component or NADPH $\alpha_2$; NAD(P)H third shortest lifetime amplitude component or NADPH $\alpha_3$; NAD(P)H mean fluorescence lifetime or NAD(P)H $\tau_m$; NAD(P)H first fluorescence lifetime or NAD(P)H $\tau_1$; NAD(P)H second fluorescence lifetime or NAD(P)H $\tau_2$; NAD(P)H third fluorescence lifetime or NAD(P)H $\tau_3$; NAD(P)H fourth fluorescence lifetime or NAD(P)H $\tau_4$; NAD(P)H fifth fluorescence lifetime or NAD(P)H $\tau_5$; FAD first amplitude component or FAD $\alpha_1$; FAD second shortest lifetime amplitude component or FAD $\alpha_2$; FAD third shortest lifetime amplitude component or FAD $\alpha_3$; FAD mean fluorescence lifetime or FAD $\tau_m$; FAD first fluorescence lifetime or FAD $\tau_1$; FAD second fluorescence lifetime or FAD $\tau_2$; FAD third fluorescence lifetime or FAD $\tau_3$; FAD fourth fluorescence lifetime or FAD $\tau_4$; and FAD fifth fluorescence lifetime or FAD $\tau_5$.

In some cases, two, three, four, five, six, seven, eight, nine, ten, or more inputs are used.

In cases where two inputs are used, those two inputs can be NAD(P)H $\alpha_1$ and cell size. In cases where three inputs are used, those three inputs can be NAD(P)H $\alpha_1$, cell size, and redox ratio. In cases where four inputs are used, those four inputs can be NAD(P)H $\alpha_1$, cell size, redox ratio, and NAD(P)H $\tau_1$. In cases where five or more inputs are used, those five or more inputs can be NAD(P)H $\alpha_1$, cell size, redox ratio, NAD(P)H $\tau_1$, and one or more of the above-referenced metabolic endpoints.

When one endpoint is used, the activation value is simply the endpoint value, which is then compared to the threshold value for the purposes of the physically isolating step. When two more endpoints are used, a mathematical formula is used to provide the activation value. This formula is a multi-variable equation that produces a single activation value. The multi-variable equation can be selected, determined, or otherwise calculated using classification and feature selection machine learning, including but not limited to, linear regression, logistic regression, random forest, support vector machines, neural networks, quadratic regression, k-means clustering, and the like.

The method 100 can sort T cells based on CD4+, CD3+, and/or CD8+ activation status.

The method 100 can provide surprising accuracy of classifying T cells as activated. The accuracy can be at least 75%, at least 80%, at least 85%, at least 90%.

Figure 2:
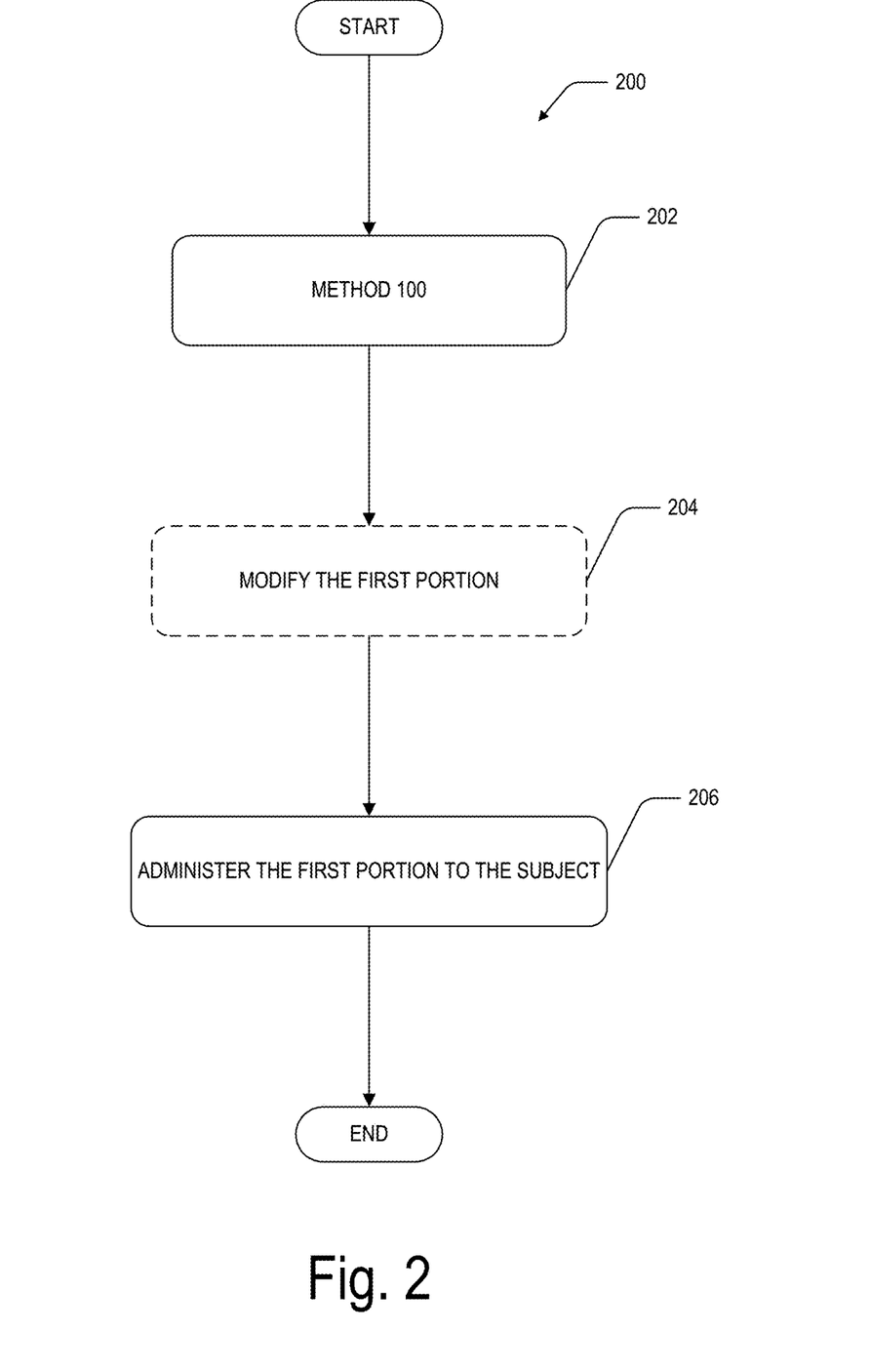
FIG. 2 is a flowchart illustrating a method, in accordance with an aspect of the present disclosure.

Referring to FIG. 2, the present disclosure provides a method 200 of administering activated T cells to a subject in need thereof. At process block 202, the method 200 includes the method 100 described above, which results in a first portion of the population of T cells enriched for activation. At optional process block 204, the method 200 optionally includes modifying the first portion of the population of T cells. At process block 206, the method 200 includes administering the first portion of the population of T cells to the subject.

The T cells can be harvested from the subject to which they are administered prior to sorting. The sorted T cells can be either directly introduced to the subject or can undergo additional processing prior to introduction to the subject. In one case, the sorted T cells can be modified to contain chimeric antigen receptors (CARs).

The methods described herein provided surprising results to the inventors in at least three ways. First, it was not clear at the outset whether the methods would be effective at distinguishing activated versus quiescent T cells, so the efficacy itself was surprising and the quality of the classification achieved by the methods was even more surprising. Second, the inventors expected different endpoints to provide the strongest classification results and were surprised when the NAD(P)H shortest lifetime amplitude component (i.e., NAD(P)H $\alpha_1$) proved to be the strongest classification endpoint. Existing methods emphasize cell size in order to determine activation state, so one might have expected cell size to play a more significant part in classification than it does in the methods described herein. To be clear, including cell size as one of the endpoints in the methods described herein does improve classification, but the inventors anticipated cell size being a larger contributor to classification accuracy. With respect to the fluorescence endpoints themselves, the inventors anticipated that the redox ratio would be the strongest contributor to classification accuracy, but surprisingly discovered that the NAD(P)H shortest lifetime amplitude component was the strongest contributor. Third, the degree of classification accuracy achieved by any single endpoint, let alone the surprising NAD(P)H shortest lifetime amplitude component, was surprising. The classification accuracy of upward of 80-90% that is achieved using only the NAD(P)H first amplitude component could not have been predicted.

Systems

This disclosure also provides systems. The systems can be suitable for use with the methods described herein. When a feature of the present disclosure is described with respect to a given system, that feature is also expressly contemplated as being combinable with the other systems and methods described herein, unless the context clearly dictates otherwise.

Figure 3:
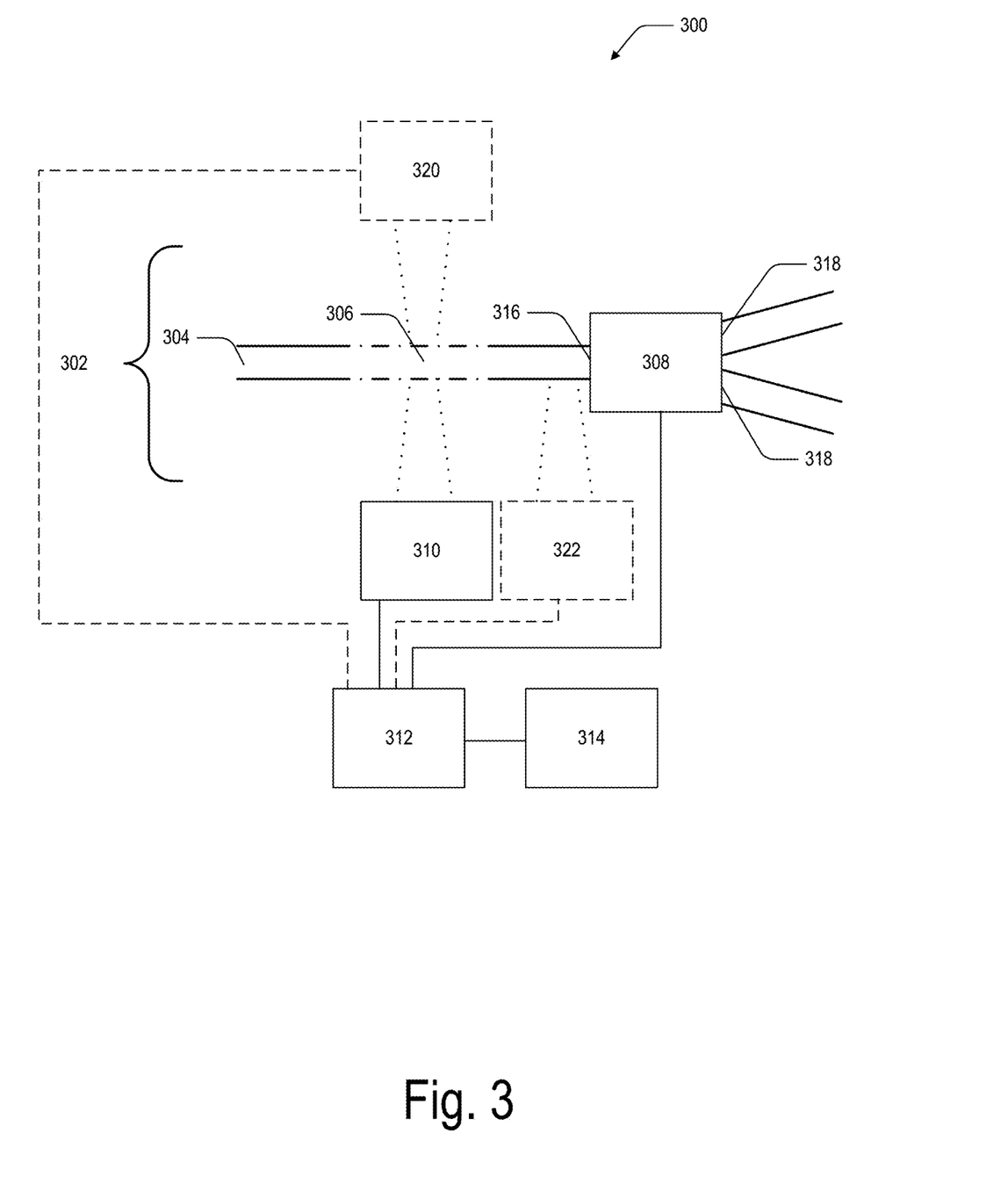
FIG. 3 is a block diagram of a device, in accordance with an aspect of the present disclosure.

Referring to FIG. 3, the present disclosure provides a T cell sorting device 300. The device 300 includes a cell sorting pathway 302. The cell sorting pathway 302 includes an inlet 304, an observation zone 306, and a cell sorter 308. The observation zone 306 is coupled to the inlet 304 downstream of the inlet 304. The device 300 also includes a single-cell autofluorescence detector 310. The device 300 includes a processor 312 and a non-transitory computer-readable medium 314, such as a memory.

The inlet 304 can be any nanofluidic, microfluidic, or other cell sorting inlet. A person having ordinary skill in the art of fluidics has knowledge of suitable inlets 304 and the present disclosure is not intended to be bound by one specific implementation of an inlet 304.

The observation zone 306 is configured to present T cells for individual autofluorescence interrogation. A person having ordinary skill in the art has knowledge of suitable observation zones 306 and the present disclosure is not intended to be bound by one specific implementation of an observation zone 306.

The cell sorter 308 has a sorter inlet 316 and at least two sorter outlets 318. The cell sorter is coupled to the observation zone 306 via the sorter inlet 316 downstream of the observation zone 306. The cell sorter 308 is configured to selectively direct a cell from the sorter inlet 316 to one of the at least two sorter outlets 318 based on a sorter signal.

The inlet 304, observation zone 306, and cell sorter 308 can be components known to those having ordinary skill in the art to be useful in flow sorters, including commercial flow sorters. The cell sorting pathway can further optionally include a flow regulator, as would be understood by those having ordinary skill in the art. The flow regulator can be configured to provide flow of cells through the observation zone at a rate that allows the single cell autofluorescence detector 310 to acquire the autofluorescence lifetime information. A useful review of the sorts of fluidics that can be used in combination with the present disclosure is Shields et al., "Microfluidic cell sorting: a review of the advances in the separation of cells from debulking to rare cell isolation," *Lab Chip*, 2015 Mar. 7; 15(5): 1230-49, which is incorporated herein by reference in its entirety.

The single-cell autofluorescence detector 310 can be any detector suitable for measuring single-cell autofluorescence as understood by those having ordinary skill in the optical arts. Examples of suitable single-cell autofluorescence detectors 310 include, but are not limited to, a photomultiplier tube, a camera, a photodiode, an avalanche photodiode, a streak camera, a charge capture device, and the like.

The single-cell autofluorescence detector 310 can be directly (i.e., the processor 312 communicates directly with the detector 310 and receives the signals) or indirectly (i.e., the processor 312 communicates with a sub-controller that is specific to the detector 310 and the signals from the detector 310 can be modified or unmodified before sending to the processor 312) controlled by the processor 312. Fluorescence lifetime information can be obtained using time-domain (time-correlated single-photon counting, gated detection) or frequency-domain methods. The device 300 can include various optical filters tuned to isolate autofluorescence signals of interest. The optical filters can be tuned to the autofluorescence wavelengths of NAD(P)H and/or FAD.

The device 300 can optionally include a light source 320 for optically exciting the cells to initiate autofluorescence. Suitable light sources 320 include, but are not limited to, lasers, LEDs, lamps, filtered light, fiber lasers, and the like. The light source 320 can be pulsed, which includes sources that are naturally pulsed and continuous sources that are chopped or otherwise optically modulated with an external component. The light source 320 can provide pulses of light having a full-width at half maximum (FWHM) pulse width of between 1 fs and 10 ns. In some cases, the FWHM pulse width is between 30 fs and 1 ns. The light source 320 can emit wavelengths that are tuned to the absorption of NAD(P)H and/or FAD.

The single-cell autofluorescence detector 310 can be configured to acquire the autofluorescence data set at a repetition rate of between 1 kHz and 20 GHz. In some cases, the repetition rate can be between 1 MHz and 1 GHz. In other cases, the repetition rate can be between 20 MHz and 100 MHz. The light source 320 can be configured to operate at these repetition rates.

The device 300 can optionally include a cell size measurement tool 322. The cell size measurement tool 322 can be any device capable of measuring the size of cells, including but not limited to, an optical microscope. In some cases, the single-cell autofluorescence detector 310 and the cell size measurement tool 322 can be integrated into a single optical subsystem.

The processor 312 is in electronic communication with the detector 310 and the cell sorter 308. The processor 312 is also in electronic communication with, when present, the optional light source 320 and the optional cell size measurement tool 322.

The non-transitory computer-readable medium 314 has stored thereon instructions that, when executed by the processor, cause the processor to execute at least a portion of the methods described herein.

Example 1

Peripheral blood was drawn from healthy donors into sterile syringes containing heparin. CD3+, CD4+, or CD8+ T cells were extracted from whole blood (RosetteSep, Stem-Cell Technologies) and cultured in T cell activation media (StemCell Technologies). Twenty-four hours post-isolation, a tetrameric antibody for CD2/CD3/CD28 was added to the culture media to activate the T cells. Activation state (CD69+) and T cell subtype (CD4+, CD8+) was verified with antibody immunofluorescence. Fluorescence intensity and lifetime images were acquired using a custom-built multiphoton fluorescence microscope (Bruker Fluorescence Microscopy, Middleton, WI) adapted for fluorescence lifetime imaging with time-correlated single photon counting electronics. T cells were imaged with a 100×objective (NA=1.3). A tunable titanium:sapphire laser provided the excitation light at 750 nm for NAD(P)H excitation and 890 nm for FAD excitation. The laser power at the sample was 3.0-3.5 mW for NAD(P)H and 5.3-5.7 mW for FAD. A bandpass filters, 440/80 nm and 550/100 nm, were used to filter NAD(P)H and FAD fluorescence emission, respectively. Fluorescence emission was detected by GaAsP PMTs, and fluorescence lifetime decays with 256 time bins were acquired for each pixel by time correlated single photon counting electronics (SPC-150, Becker & Hickl, Berlin, Germany). The second harmonic generation from red blood cells was used as the instrument response function and had a full width at half maximum of 240 ps. Fluorescence lifetime decays were deconvolved from the instrument response function and fit to a 2 component exponential decay model, $I(t)=\alpha_1*\exp(-t/\tau_1)+\alpha_2*\exp(-t/\tau_2)+C$, where $I(t)$ is the fluorescence intensity as a function of time, t, after the laser pulse, $\alpha_1$ and $\alpha_2$ are the fractional contributions of the short and long lifetime components, respectively (i.e., $\alpha_1+\alpha_2=1$), $\tau_1$ and $\tau_2$ are the short and long lifetimes, respectively, and C accounts for background light. NAD(P)H intensity images were segmented into cytoplasm, mitochondria, and nucleus using edge detect and thresholding methods in CellProfiler using a customized image processing routine. Images of the optical redox ratio (fluorescence intensity of NAD(P)H divided by the summed intensity of NAD(P)H and FAD) and mean fluorescence lifetime ($\tau_m=\alpha_1*\tau_1+\alpha_2*\tau_2$) of NAD(P)H and FAD were computed (Matlab). OMI endpoints, including the optical redox ratio, NAD(P)H $\tau_m$, NAD(P)H $\tau_1$, NAD(P)H $\tau_2$, NAD(P)H $\alpha_1$, FAD $\tau_m$, FAD $\tau_1$, FAD $\tau_2$, and FAD $\alpha_1$ were averaged across all pixels within a cell for each segmented cell. Cell size in $\mu m^2$ was also computed from the number of pixels within the cell.

The results show a significant increase ($p<0.001$) in cell size, optical redox ratio, NAD(P)H $\alpha_1$, FAD $\alpha_1$, and NAD(P)H $\tau_1$ between quiescent and activated CD3+ and CD8+ T cells across 6 donors. NAD(P)H $\tau_m$, and FAD $\tau_1$ were significantly ($p<0.001$) decreased in activated CD3+ and CD8+ T cells as compared to quiescent T cells. FAD $\tau_m$ was significantly decreased in activated CD3+ T cells as compared with quiescent CD3+ T cells, but no significant difference in FAD $\tau_m$ was observed between quiescent and activated CD8+ T cells. NAD(P)H $\tau_2$ was significantly increased in activated CD3+ T cells as compared to quiescent CD3+ T cells and significantly decreased in activated CD8+ T cells as compared to quiescent CD8+ T cells. FAD $\tau_2$ was significantly increased in activated CD3+ T cells as compared to quiescent CD3+ T cells, and no significant difference was observed in FAD $\tau_2$ between quiescent and activated CD8+ T cells. Similar results were obtained for T cells cultured with the activation antibodies for 24 hours. Consistent results were obtained from a repeat experiment on the T cells of one donor The CD3+ and CD8+ quiescent and activated data sets were divided into training and testing data for classification: cells from 4 donors known to be quiescent or activated by culture conditions were used to train the models (n=4131 CD3+ cells, 2655 CD8+ cells) and cells from 3 donors with same-cell CD69 validation of activation state were used to test the models (n=696 CD3+ cells, 595 CD8+ cells). Gain ratio, random forest, and Chi-squared methods for weighting features revealed NAD(P)H $\alpha_1$ as the most important feature for classification of activation state of CD3+ and CD8+ T cells. For CD3+ T cells, the gain ratio determined order of importance of features was NAD(P)H $\alpha_1$, cell size, redox ratio, NAD(P)H $\tau_1$, FAD $\alpha_1$, NAD(P)H $\tau_m$, FAD $\tau_2$, FAD $\tau_1$, NAD(P)H $\tau_2$, and FAD $\tau_m$. For CD8+ T cells, the gain ratio determined order of importance of features was NAD(P)H $\alpha_1$, redox ratio, NAD(P)H $\tau_m$, cell size, NAD(P)H $\tau_2$, FAD $\tau_1$, FAD $\tau_m$, FAD $\tau_2$, NAD(P)H $\tau_1$, and FAD $\alpha_1$. A logistic regression classification model, yielded accuracies of 97.5%, 70.8%, 96.5%, 90.1%, 97.1%, and 93.9% for the classification of CD3+ T cells as activated or quiescent when trained on all 10 features; cell size only; NAD(P)H $\alpha_1$ only; redox ratio and cell size; redox ratio, cell size and NAD(P)H $\alpha_1$; and redox ratio, NAD(P)H $\tau_m$ and NAD(P)H $\alpha_1$. A logistic regression classification model yielded accuracies of 99.6%, 68.7%, 99.4%, 95.7%, 99.9%, and 98.4% for the classification of CD8+ T cells as activated or quiescent when trained on all 10 features; cell size only; NAD(P)H $\alpha_1$ only; redox ratio and cell size; redox ratio, cell size and NAD(P)H $\alpha_1$; and redox ratio, NAD(P)H $\tau_m$ and NAD(P)H $\alpha_1$. Similar accuracies (~94-99%) were achieved with different classification models including random forest and support vector machines when trained with all 10 features. No improvement in classification accuracy was achieved by training and testing with donor normalized data.

All prior results were for quiescent and activated T cells grown in isolated dishes. To ensure this method is robust at distinguishing activated from not activated T cells in mixed populations, we evaluated quiescent and activated T cells that were cultured separately for 48 hours and then mixed into co-culture one hour before imaging. Mixed co-culture of quiescent and activated T cells causes some changes in the autofluorescence endpoints. For example, the redox ratio was significantly decreased in activated CD3+ T cells in mixed co-cultures of activated and quiescent T cells as compared to that of activated CD3+ T cells cultured without quiescent T cells. NAD(P)H $\alpha_1$ was significantly increased in activated CD3+ T cells in mixed cultures of activated and quiescent T cells and remained the most important feature (~0.35 normalized weight) for classification, as determined by random forest feature selection methods. NAD(P)H $\tau_m$ and NAD(P)H $\tau_2$ were the second and third most important features with normalized weights of ~0.22 and ~0.1. Logistic regression classification of quiescent and activated T cells within mixed cultures yielded accuracies of 95.5%, 76.6%, 100%, and 72.7% when trained on all 10 features, cell size only, NAD(P)H $\alpha_1$ only, and redox ratio and cell size, respectively.

We claim:
1. A T cell sorting device comprising:
   a cell sorting pathway comprising:
      (i) an observation zone comprising a fluidic channel, the observation zone configured to present T cells for individual autofluorescence interrogation; and
      (ii) a cell sorter having a sorter inlet and at least two sorter outlets, the cell sorter coupled to the observation zone via the sorter inlet downstream of the observation zone, wherein the cell sorter configured to selectively direct a cell from the sorter inlet to one of the at least two sorter outlets based on a sorter signal;
   a single-cell autofluorescence detector comprising a light detector, the single-cell autofluorescence detector configured to acquire an autofluorescence data set from a T cell positioned in the observation zone, the single-cell autofluorescence detector configured to acquire autofluorescence lifetime information for each autofluorescence data set, wherein the autofluorescence data set comprises at least one metabolic endpoint;
   a light source for illuminating the observation zone;

a processor in electronic communication with the cell sorter and the single-cell autofluorescence detector; and a non-transitory computer-readable medium having stored thereon instructions that, when executed by the processor, cause the processor to:

a) receive the autofluorescence data set; and b) provide the sorter signal to the cell sorter based on an activation value, wherein the sorter signal directs the cell sorter to selectively direct the T cell to a first outlet of the at least two sorter outlets when the activation value exceeds a predetermined threshold and to a second outlet of the at least two sorter outlets when the activation value is less than or equal to the predetermined threshold, wherein the activation value is computed by the processor based on at least one metabolic endpoint of the autofluorescence data set for the T cell as an input, wherein the at least one metabolic endpoint includes reduced nicotinamide adenine dinucleotide (NAD(P)H) shortest fluorescence lifetime amplitude component ($\alpha 1$), and wherein the activation value is computed using an equation generated by a machine learning process and autofluorescence data for a population of T cells having a known activation state and using the at least one metabolic endpoint as a variable.

2. The T cell sorting device of claim 1, wherein the cell sorting pathway comprises a microfluidic pathway or a nanofluidic pathway.

3. The T cell sorting device of claim 1, the light source further comprising a pulsed light source having a full width at half maximum pulse width of between 1 fs and 10 ns.

4. The T cell sorting device of claim 1, wherein the single-cell autofluorescence detector is configured to acquire the autofluorescence data set at a repetition rate of between 1 kHz and 20 GHz.

5. The T cell sorting device of claim 1, wherein the single-cell autofluorescence detector is configured to acquire the autofluorescence data set via time-correlated single photon counting.

6. The T cell sorting device of claim 1, wherein the single-cell autofluorescence detector is a photomultiplier tube or a photodiode.

7. The T cell sorting device of claim 1, the T cell sorting device further comprising a cell size measurement tool configured to measure cell size and to communicate the cell size to the processor.

8. The T cell sorting device of claim 7, wherein the activation value is computed using the cell size for each T cell of the population of T cells as an input.

9. The T cell sorting device of claim 1, wherein the at least one metabolic endpoint further includes an endpoint selected from the group consisting of optical redox ratio, NAD(P)H mean fluorescence lifetime ($\tau m$), NAD(P)H first fluorescence lifetime component ($\tau 1$), NAD(P)H second fluorescence lifetime component ($\tau 2$), flavin adenine dinucleotide (FAD) $\tau M$, FAD $\alpha 1$, FAD $\tau 1$, FAD $\tau 2$, and combinations thereof.

* * * * *

UNITED STATES PATENT AND TRADEMARK OFFICE
CERTIFICATE OF CORRECTION

| | |
|---|---|
| PATENT NO. | : 12,023,676 B2 |
| APPLICATION NO. | : 17/855929 |
| DATED | : July 2, 2024 |
| INVENTOR(S) | : Melissa Caroline Skala et al. |

It is certified that error appears in the above-identified patent and that said Letters Patent is hereby corrected as shown below:

In the Specification

Column 8, Line 67, "100×objective" should be --100× objective--.

Column 12, Line 27, "τM" should be --τm--.

Signed and Sealed this
Sixth Day of August, 2024

Katherine Kelly Vidal
*Director of the United States Patent and Trademark Office*